United States Patent [19]
Achatz et al.

[11] 4,159,867
[45] Jul. 3, 1979

[54] DEVICE AND METHOD FOR MEASURING THE CURVATURE OF THE CORNEA

[75] Inventors: Manfred Achatz, Heusenstamm; Rasmus Beck, Neu-Isenburg; Werner Bockelmann, Frankfurt am Main, all of Fed. Rep. of Germany

[73] Assignee: Battelle-Institute e. V., Frankfort am Main, Fed. Rep. of Germany

[21] Appl. No.: 831,996

[22] Filed: Sep. 9, 1977

[30] Foreign Application Priority Data

Sep. 11, 1976 [DE] Fed. Rep. of Germany ....... 2641004

[51] Int. Cl.² .......................... A61B 3/10; A61B 3/00
[52] U.S. Cl. ........................................ 351/6; 351/39; 351/13
[58] Field of Search ........................... 351/6, 13, 39, 16

[56] References Cited

U.S. PATENT DOCUMENTS 3,542,458  11/1970  Volk ....................................... 351/39

Primary Examiner—Paul A. Sacher
Assistant Examiner—Rodney Bovernick
Attorney, Agent, or Firm—Fisher, Christen & Sabol

[57] ABSTRACT

A device and method are disclosed for measuring the curvature of the cornea of the human eye. The device utilizes a continuous, curved surface plate positioned in front of the eye and having a telescope extending through the surface plate such that its optical axis is aligned with the eye. Several object points are generated on the surface plate within the field of vision of the eye and are formed also on the image plane of the eye. Detection devices, located within the telescope measure the positions of such image points in relation to the optical axis. The radius of curvature of the cornea can be determined from this measurement.

13 Claims, 2 Drawing Figures

DEVICE AND METHOD FOR MEASURING THE CURVATURE OF THE CORNEA

FIELD OF THE INVENTION

The present invention relates to a device and method of automatically measuring the curvature of the cornea.

BRIEF DESCRIPTION OF THE PRIOR ART

Measurements of the curvature radius of the front surface of the cornea provide information about the curvature of the cornea and corneal astigmatism. Since the astigmatism in the refraction of the eye must be known, instruments for measuring the curvature radii of the front surface of the cornea, so-called keratometers, have been used in ophthalmology for prescribing spectacles. Since the introduction of corneal contact lenses, this measurement must be carried out as a matter of routine since an accurate knowledge of the curvature of the cornea is necessary for the exact fit of a contact lens on the cornea. When making the fit it should be borne in mind that the surface of the cornea is not a single spherical segment of constant curvature, but towards the edge it flattens out to a varying extent. Apart from this, attention should be paid to the fact that there is normally an astigmatism of the front surface of the cornea. Instruments for keratometrical measurements are known. They involve measuring the size of the corneal ghost image, the so-called 1st Purkinje image, as compared to a given object. In the case of older equipment this is done visually by measuring the size of the image in an eyepiece micrometer. In this equipment the surface for recording the object points consists of two pivoting curved arms which permit the formation of image points on only one axis, and only on another axis when the equipment is rotated.

Newer developments comprise photokeratometers with four arms standing mutually at right angles, with the aid of which the image projected on to the cornea is photographed and analyzed densitometrically. With these photokeratometers it is possible to obtain the necessary values from a single recording, but they have the crucial disadvantage that the recording must be analyzed at a central collecting point which has all the necessary equipment, e.g. densitometer, computer, etc. For this reason there is, more often than not, an unreasonable passage of time between the actual measurement and the receipt of the result.

SUMMARY OF THE INVENTION

The aim of the present invention is to develop a device and a method for automatically measuring the curvature of the cornea, so that the ophthalmologist or optician will be able to measure the desired data quickly and in as practical a form as possible. The device according to the invention, has a continuous surface plate having means for generating object points; a telescope centered on this surface, the telescope having an attachment between the eyepiece and the objective lens for reflecting the light incident in the telescope; and a detector disposed so as to detect the light reflected by this attachment. This device can be used to measure the curvature of the cornea automatically by connecting the detector to a microcomputer, a temporary storage device and an output unit.

DETAILED DESCRIPTION OF THE PREFERRED EMBODIMENT

Figure 1:
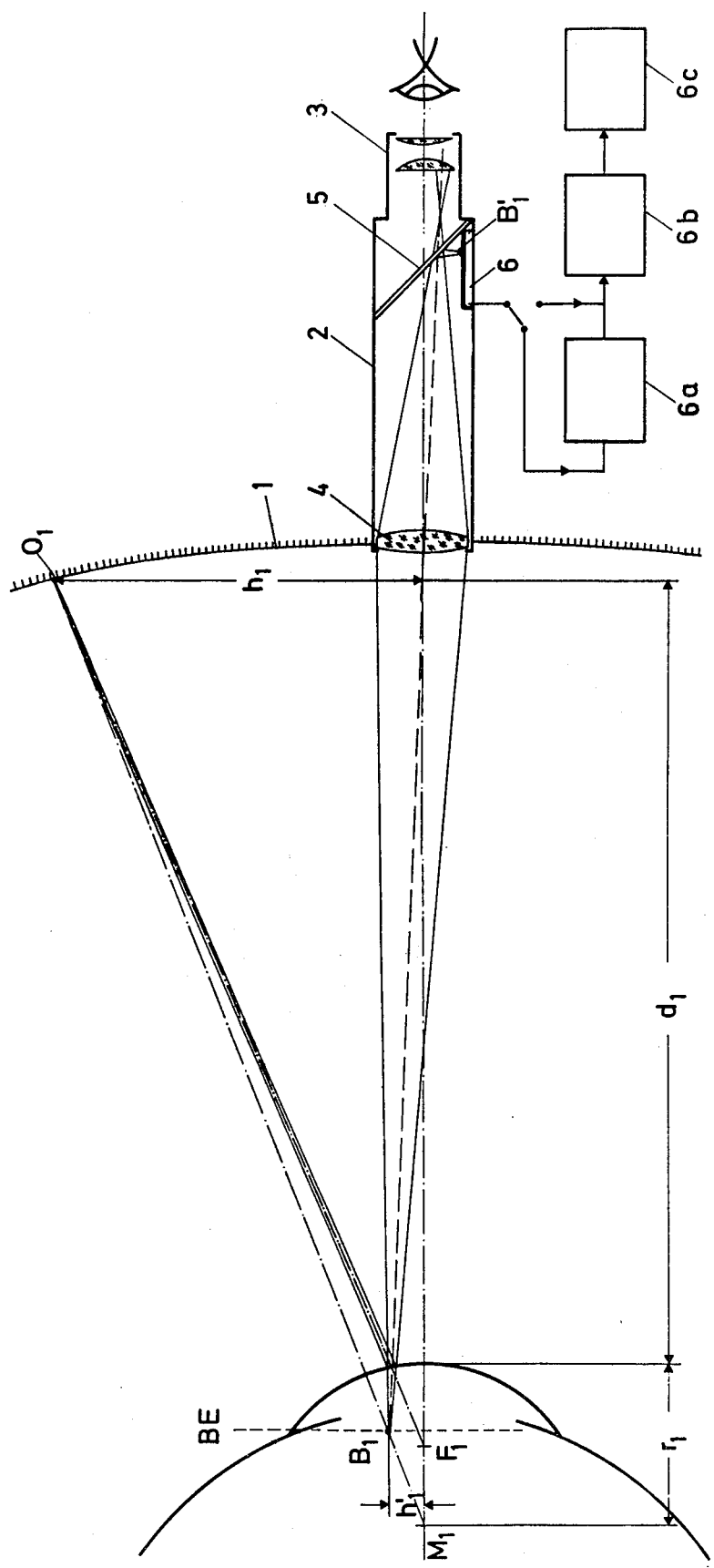
FIG. 1 shows a schematic diagram of a corneal measuring device according to the invention.

As can be seen from FIG. 1, the device according to the invention consists of an object surface plate 1 (having means for generating object points $O_i$) which should preferably be in the form of a curved or cardioid surface, and a telescope 2 located in the center of this surface. A cardioid surface corresponding to $R=r_o\cdot(1+\cos\phi)$ is preferred, since then the virtual image surface behind the cornea is even. But the object surface plate 1 can also have other curvatures which must then be taken into consideration by corrections in the evaluation.

The material from which the object surface plate is made depends upon the type of light source used to form the object points. The telescope 2 centered on object surface plate 1 has an attachment 5 between eyepiece 3 and objective lens 4 which serves, for the main part, to reflect the light incident in the telescope. This attachment 5 can be a hinged mirror or a partially light transmitting mirror. Partially light-transmitting mirrors are preferable since they allow the observer to look through the mirror to adjust the position of the telescope without moving the mirror out of the light path through the telescope. If, however, a hinged mirror is used, then the device for the telescope must include an attachment with which the hinged mirror can be moved out of the light path. This is necessary since the hinged mirror must be removed from the light path by observer in order to align the telescope prior to the actual measurement. The telescope has in addition, a detector 6, which is positioned to receive the light reflected by the partially light-transmitting mirror or the hinged mirror, and which is itself linked with a computer 6b either directly, or using a temporary storage device 6a. The established values are indicated, via output electronics 6c coupled to the outlet side of the computer.

The detector 6, which serves to detect and measure the image distance $h_i$ from the optical axis, should preferably be a position-sensitive silicon detector. A further possibility is offered by the use of a vidicon as the recording element. Linear diode arrays, or a diode matrix could also be used as detectors. The linear diode arrays, the diode matrix and the vidicon can process all the image points operating simultaneously, whereas the position-sensitive silicon detector requires sequential operation of the object point generating means.

According to the method of the present invention light points or object points $O_i$ are formed on the curved object surface plate 1 at different sites. The reflections of these points, which light up in the image plane BE, can be regarded as virtual images $B_i$, as so-called 1st Purkinje images, and their positions can be measured in relation to the optical axis.

For centering the telescope on the object to be measured or for adjusting the measuring apparatus according to the invention, it is preferable to generate four streaks of light or alignment streaks 7 on the object surface in the direction of the two perpendicular axes. The Purkinje images of these, observed in their entirety through the eyepiece, lie on two straight lines which cross each other, when the adjustment is correct.

The alignment streaks are preferably generated in a manner similar to the generating of the object points $O_i$ to be described hereinafter. These alignment streaks 7 are represented schematically in FIG. 2. The proposed method of adjustment has the advantage that it is considerably more precise than other methods due to the vernier visual acuity in the adjustment of the axes. Following this, the four alignment streaks are extinguished and the actual measuring procedure is initiated. The maximum time for the measuring procedure is the time between two blinks.

There are various possibilities for generating light points $O_i$ or alignment streaks 7 on the object plane 1. Diaphragms lighted up from behind, light guiding assemblies (glass fibres), point light sources (e.g. laser diodes) or a movable light point (flying spot) produced by laser light and deflection unit, can be used for this purpose.

The greatest coverage of the measuring field with light marks is obtained by the formation of light marks by means of flying spots. Here the object point $O_i$ can be transversed via any route, over the object surface 1 by the appropriate control of the deflection unit. The formation of light marks via diaphragms lighted up from behind and via point light sources (e.g. laser diodes) permit both simultaneous and sequential illumination. Only sequential illumination measurement is possible with flying spot illumination. If an object point $O_i$ is formed on the object surface 1 then its reflection is observed as a virtual image $B_i$ on the dotted image plane BE. The radius of curvature of the cornea $r_1$ for this special object point and thus for the corresponding segment of the cornea with the mid-point of curvature $M_i$, is then given by the following formula, e.g. for the object point $O_1$:

$$r_1 = 2d_1(h_1'/h_1)$$

Where $h_1$ is the distance of the object point $O_1$ and $h_1'$ is the distance of the image point $B_1$ from the optical axis. The distances $d_1$ and $h_1$ are known from the geometrical relationships of the configuration. The measurement of $h_1'$ by means of detectors thus supplies the curvature radius of the cornea.

In deriving the above formula, the fact that the virtual image lies approximately in front of the focus $F_1$ of the convex mirror formed by the cornea can be neglected since the distance $d_1$ is large in comparison with the distance between the virtual image plane BE and $F_1$.

An enlarged image of the image point $B_1$ is produced on the detector by the reflection from attachment 5 and this determines the position of the secondary image point $B_1'$. The detector 6 produces a measuring signal, which essentially consists of the ratio of the object height $h_1$ to image height $h_1'$, which, in turn is converted into the radius of curvature $r_1$ by a computer 6b which is linked to the detector 6, after the necessary corrections have been made. All the radii measured at all the object points either simultaneously or sequentially, thus represent the curvature of the surface of the cornea.

The application of telescopic optics is necessary to compensate for the low depth of focus of the image formation needed for this special measuring task. Thus, when carrying out the measurement, it is possible to correctly maintain the working distance automatically between the measuring optics and the image plane BE, if the secondary image points $B_1'$ are sharply imaged on the receiving surface.

The telescope 2 should have as small a diameter as possible and be located in the plane of the cardiods.

This small diameter ensures that object points $O_i$ formed close to the central axis are not obscured by the image-forming optics, and also that the divergence of the beam of light picked up, and hence the spot size of the appropriate segment of the cornea, is as small as possible. The object points $O_i$ should cover as large an area of the visual angle as possible (e.g. $3° \leq \theta \leq 45°$).

The position coordinates of the image points $B_1'$ can be fed into computer 6b, either directly or using temporary storage device 6a, from which it calculates from the coordinates, the curvature in the particular segments of the cornea illuminated.

In this way the contact lens fitter is able to determine the optimal coaxial radii of the cornea being measured, by means of appropriate realtime reporting procedures or, if required, he can also determine the total curvature profile of the front surface of the cornea.

Figure 2:
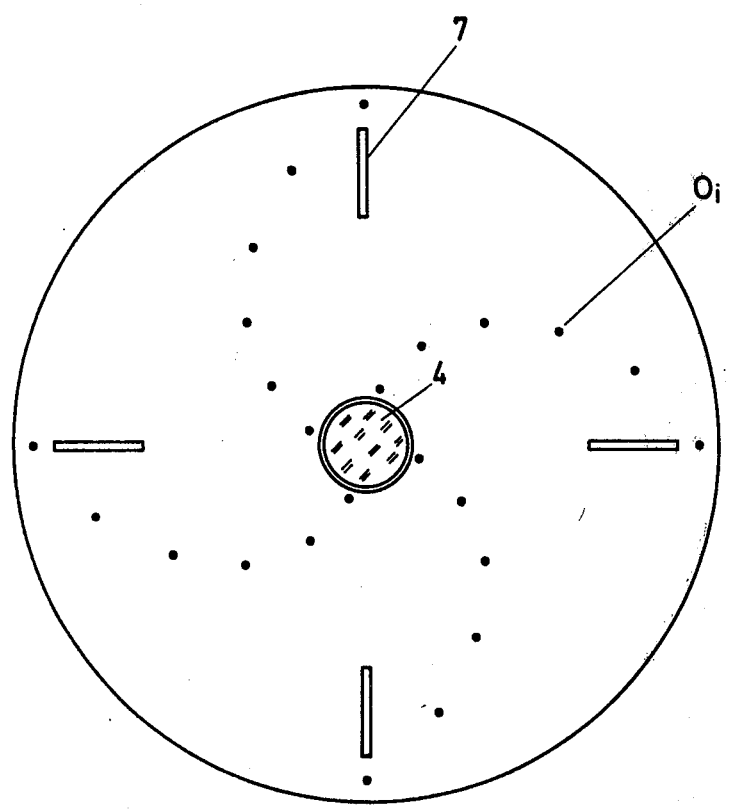
FIG. 2 is a front view of the continuous surface of the device of FIG. 1.

The object points $O_i$ on the object surface 1 can be arranged in the simplest case in the form of a cross. FIG. 2, however, shows especially advantageous configuration in the form of a multiple-beam Archimedean spiral which results from the sequential method of operation of the present invention.

A commercial helium-neon laser, for example, with a low output power of about 1 mW is sufficient for generating object points. In this case it is advantageous if the surface plate for the object points consists of a light-transmitting material so that the relevant setup can be positioned behind the surface plate. The laser beam is guided accross the surface plate via a deflecting means, e.g. an electromechanically driven pivoting mirror.

If point light sources are used for generating the object points, a sufficient number of them can be firmly attached to the surface plate. This is achieved, e.g., by cementing, countersinking, screwing commercial laser diodes on to or into the surface of the support.

When generating the object points with light guiding assemblies such as glass fibres, the surface plate must be provided with an adequate number of holes in which the individual light guides end. At their other end these light guides are illuminated by a single common light source. Object points can also be generated by illuminating a large area of the surface plate provided with holes from behind.

We claim:
1. A device for measuring the curvature of a cornea comprising:
 (a) a continuous surface plate positioned in front of the cornea to be measured;
 (b) a telescope extending through said continuous surface plate having its optical axis located at the center of said surface;
 (c) means to generate a plurality of object points on said surface plate, the object points forming image points on the image plane of the cornea;
 (d) reflecting means in said telescope for reflecting incident light from the image plane of the cornea;
 (e) detecting and measuring means for detecting the light reflected by said reflecting means and for measuring the position of the image points with respect to the optical axis to thereby determine the curvature of the cornea.

2. The device according to claim 1 wherein the surface plate is curved.

3. The device according to claim 2 wherein the curved surface plate has a cardiod curvature.

4. The device according to claim 1 wherein the reflecting means is a mirror pivotally attached to the telescope.

5. The device according to claim 1 wherein the reflecting means is a partially light transmitting mirror.

6. The device according to claim 1 wherein the detecting and measuring means comprises:
   (a) a detector in said telescope positioned so as to receive incident light reflected by said reflecting means and to generate an output signal in response to the position of said light; and
   (b) a computer connected to said detector so as to receive said output signals therefrom and to calculate the curvature of said cornea in response to said signals.

7. The device according to claim 6 further comprising a temporary storage device interposed between and connected to said detector and said computer.

8. The device according to claim 6 wherein said detector is a position-sensitive detector.

9. The device according to claim 1 wherein the surface plate is sized so as to project object points to the eye at an angle of betweeen 3° and 45°.

10. The device according to claim 1 wherein the means to generate the object points comprises a laser light source and means to deflect the light generated by said laser light source onto said surface plate.

11. A method of measuring the curvature of a cornea comprising the steps of:
   (a) generating a plurality of object points on a continuous surface plate positioned in front of the eye;
   (b) measuring the location of the reflections of said object points on the image plane of the cornea in relation to the optical axis of a telescope located in the center of said surface plate; and
   (c) determining the curvature of the cornea from the measured distance between the object points and the optical axis.

12. The method according to claim 11 comprising the additional steps of:
   (a) generating a plurality of light streaks on said continuous surface plate; and,
   (b) positioning said telescope by adjusting it such that the light streaks form two straight lines which cross each other on the image plane of the cornea.

13. The method according to claim 11 wherein the plurality of object points are produced in the form of a multi-beam Archimedean spiral.

* * * * *